United States Patent [19]

Kaufhold

[11] Patent Number: 4,944,848

[45] Date of Patent: Jul. 31, 1990

[54] PROCESS FOR THE PURIFICATION OF 1,1-DIPHENYLETHANE WITH GOOD FRAGRANCE QUALITY

[75] Inventor: Manfred Kaufhold, Marl, Fed. Rep. of Germany

[73] Assignee: Huels Aktiengesellschaft, Marl, Fed. Rep. of Germany

[21] Appl. No.: 410,408

[22] Filed: Sep. 21, 1989

[30] Foreign Application Priority Data

Nov. 4, 1988 [DE] Fed. Rep. of Germany ....... 3837450

[51] Int. Cl.$^5$ .............................................. B01D 3/00
[52] U.S. Cl. ........................................ 203/35; 203/37; 203/80; 585/400; 585/700
[58] Field of Search ...................... 203/35, 37, 80, 73, 203/43, 79; 585/400, 700

[56] References Cited

U.S. PATENT DOCUMENTS

| | | | |
|---|---|---|---|
| 2,563,628 | 8/1951 | Viles | 203/35 |
| 3,631,211 | 12/1971 | Schmerling | 585/422 |
| 3,679,760 | 7/1972 | Schmerling | 568/744 |
| 3,870,659 | 3/1975 | Bozzato et al. | 585/360 |
| 3,929,676 | 12/1975 | Chappell et al. | 585/360 |
| 3,929,677 | 12/1975 | Hall et al. | 585/947 |
| 4,011,274 | 3/1977 | Watanabe | 585/423 |
| 4,033,829 | 7/1977 | Higgins, Jr. et al. | 203/35 |
| 4,435,251 | 3/1984 | Takeda et al. | 203/91 |

FOREIGN PATENT DOCUMENTS

| | | |
|---|---|---|
| 0098677 | 1/1984 | European Pat. Off. . |
| 0045114 | 3/1982 | Japan .................... 585/400 |

OTHER PUBLICATIONS

Mamedov, "Role of 1,1-diphenyethane in the disproportionation of ethylbenzene . . . " Chem. Abst. vol. 73, 1970; 120212z.

Equivalent to German Patent No.2401373 cited in the instant spec. p. 3.

Perfume and Flavor Chemicals (Aroma Chemicals) NR 2007; Methyl Diphenyl Methane, Steffen Arctander.

Chem. Berichte, (1932), 65, pp. 1686–1688, "Ueber Anlagerungsprodukte Von Styrol an Aromatische Kohlenwasserstoffe" A. Spilker et al.

*Primary Examiner*—Virginia Manoharan
*Attorney, Agent, or Firm*—Oblon, Spivak, McClelland, Maier & Neustadt

[57] ABSTRACT

A process for the purification of 1,1-diphenylethane with good fragrance quality. The product is produced by first subjecting the distillation residue from ethylbenzene production to distillation, then treating the distillate with sulfuric acid, separating the sulfuric acid phase, washing the oil phase with an alkali metal hydroxide solution and water, and subjecting the oil phase thus obtained to a second distillation.

13 Claims, No Drawings

PROCESS FOR THE PURIFICATION OF 1,1-DIPHENYLETHANE WITH GOOD FRAGRANCE QUALITY

BACKGROUND OF THE INVENTION

Field of the Invention

The invention relates to 1,1-diphenylethane and process for its preparation.

Discussion of the Background 1,1-Diphenylethane, also known as methyldiphenylmethane, is a familiar but economically unimportant odorant. It was described by Steffen Arctander (S. Arctander, Perfume and Flavor Chemicals, published by the Author 1969, Montclair, N.J. (USA), No. 2007.

One known synthesis of this odorant is based on the Friedel-Crafts reaction of styrene with benzene (see Spilker and Schade, Chem. Berichte, 65 (1932), 1686. The product 1,1-diphenylethane was obtained in only 25% yield. Other procedures described in the literature, for example the reaction of benzyl chloride with toluene and cupric chlorides as catalysts (U.S. Pat. No. 3,679,760) or the oxidative coupling of ethylbenzene and benzene with a catalyst consisting of aluminum and cupric chlorides (U.S. Pat. No. 3,631,211) produce only low yields and/or require costly starting materials, so that industrial use is not practical.

For economic reasons, on the other hand, procedures by which 1,1-diphenylethane might be obtained from the distillation residue of ethylbenzene production are of greater interest (see EP-A 98 677, Chem. Abstr. 73(23): 120212z and Chem. Abstr. 94 (20): 167136b.

As seen from EP-A 98 677, however, pure 1,1-diphenylethane cannot be obtained in this way since a number of impurities have very similar boiling points. Production of 1,1-diphenylethane with good fragrance quality from the distillation residue of ethylbenzene production is difficult for this reason.

Therefore, a need continues to exist for a simple and economical process for the production of 1,2-diphenylethane with good fragrance quality.

SUMMARY OF THE INVENTION

Accordingly, one object of this invention is a process for the production of 1,1-diphenylethane with good fragrance quality from the distillation residue of ethylbenzene production.

This and other objects, which will become apparent from the following specification have been achieved by the present process in which the distillation residue of ethylenebenzene production is subjected to a first distillation, in which a product of about 60 to 90% purity is obtained. This distillate is treated with concentrated sulfuric acid at temperatures of from about $-10°$ to $+50°$ C., the sulfuric acid phase is separated, the oil phase is washed with a hydroxide solution and then water, and a second distillation is carried out.

DETAILED DESCRIPTION OF THE PREFERRED EMBODIMENTS

From the olfactory viewpoint, the distillation residue of ethylbenzene production has an unpleasant industrial odor reminiscent of tar. When the residue is purified by costly fractional distillation, as described in detail in DE-OS 24 01 373, fractions are obtained with contents of 1,1-diphenylethane of about 82 to 92%. The technical expense is very high in this distillation and the yield of distillate is very low. The fragrance quality of the fractions is not significantly better than that of the starting material and does not conform to the quality of a conventional odorant.

Surprisingly, pursuant to the present invention, 1,1-diphenylethane with good fragrance quality is obtained in a simple way from the distillation residue of ethylbenzene production by carrying out the following purification steps: (1) a first distillation; (2) washing the distillate with sulfuric acid, alkali metal hydroxide solution, and water; and (3) a second distillation.

While repeated distillations do not lead to improvements of odor, even a simple water scrubbing brings about a sharp reduction of the tar odor. Washing with an alkali metal hydroxide solution, such as a sodium hydroxide or potassium hydroxide solution, is more effective, and the best results are achieved by treatment with sulfuric acid followed by washing with an alkali metal hydroxide, preferably sodium hydroxide, solution and water.

For further quality improvement, the washed, cloudy, light yellow oil phase is distilled in a third step. Surprisingly, foreruns with unpleasant odors are obtained in this second distillation, which can be separated and removed. The main distillate then has good fragrance quality. The odor has hardly any of the harsh, metallic characteristic noted by Arctander, but is soft and "round".

The first distillation is a simple or fractional distillation at ambient pressure or under a moderate vacuum of from about 1–200, preferably about 10–50 mbar in which a purified product (60 to 90-100 wt. %) is obtained. For example, using a vacuum of about 30 mbar, a product having a boiling range of about 150° to 170° C., preferably from 153° to 161° C. is obtained, which generally contains 60 wt. % or more 1,1-diphenylethane, and preferably more than 80 wt. %. The temperature at which the distillation is conducted is not critical. The distillation should be conducted at a temperature below the decomposition temperature of 1,2-diphenylethane, generally below about 300° C. and preferably not higher than 250° C.

The distillate is first stirred at temperatures of $-10°$ C. to $+50°$ C., preferably 0° to 20° C., with a sulfuric acid having a concentration of about 85 to 95% by weight, for a period of from about 10 minutes to 5 hours, preferably about 1 to 2 hours. For neutralization, the oil phase is then washed with a dilute, 1-25 wt. %, preferably 5-10 wt. % aqueous solution of an alkali metal hydroxide, preferably sodium hydroxide solution and then with water to remove excess hydroxide.

The cloudy, light yellow oil phase obtained is distilled again, during which it is only necessary to separate a forerun, since this has an unpleasant odor. The amount of forerun can readily be determined by one skilled in the art.

The second distillation may also be conducted at ambient pressure or under a vacuum to prevent unnecessary decomposition of the product and is conducted under conditions similar to the first distillation. Preferred distillations are conducted at moderate vacuums of from about 1-200 mbar. The boiling range of the product of the second distillation, after removal of the forerun, is in the range of 153°-161° C. These temperatures will of course depend on the pressure used during the second distillation as in the first distillation. The second distillation produces a product distillate which may contain greater than 85 wt % 1,1-diphenylethane.

The present invention provides an efficient process for the preparation of 1,1-diphenylethane having a surprisingly good odorant quality and which is particularly valuable due to its chemical stability. The present invention is a process for the efficient, economical production of an industrially important odorant.

Other features of the invention will become apparent in the course of the following descriptions of exemplary embodiments which are given for illustration of the invention and are not intended to be limiting thereof.

EXAMPLE

1. First distillation

The first distillation was carried out in a glass column 0.5 m long packed with column packing. For simplicity, the fractions were separated by boiling points. The amount of starting material (distillation residue of ethylbenzene production) for the distillation was 1000 g.

| Fraction No. | Temp. in °C. Head | Bottoms | Pressure (mbar) | Weight (g) | Reflux ratio |
|---|---|---|---|---|---|
| 1 | 119–150 | 161–176 | 30 | 164 | 1:1 |
| 2 | 150–153 | 176–183 | 30 | 21 | 1:1 |
| 3 | 153–158 | 183–185 | 30 | 207 | 1:1 |
| 4 | 158 | 185–190 | 30 | 100 | 1:1 |
| 5 | 158–161 | 190 | 30 | 37 | 1:1 |
| Residue | | | | 470 | |
| | | | Total = | 999 | |

Gas chromatographic (GC) analyses of fractions 1 to 5 showed the following contents of 1,1-diphenylethane (DPE) and of the somewhat higher-boiling 1,2-diphenylethane, also known as bibenzyl (BBZ):

| Fraction No. | DPE | BBZ |
|---|---|---|
| 1 | Not analyzed, discarded | |
| 2 | 34.7 | <0.1 |
| 3 | 83.3 | 0.4 |
| 4 | 92.3 | 1.4 |
| 5 | 82.6 | 5.8 |

The residue and fractions 1 and 2 were discarded. Since the content of DPE in fractions 3 to 5 was greater than 80%, they were combined and processed further.

Yield of distillate: 34 wt. %

2. Washing

The purification described below was carried out with DPE of approximately 80% purity. Starting material: 600 ml = 598 g DPE (80%); 50 ml = 86 g $H_2SO_4$ technical (90%)

The DPE starting material was cooled to 10° C. with stirring and the sulfuric acid was added slowly over a period of 10 minutes. Stirring was then continued for 2 hours at 10° C. In the following phase separation, 88 g of the sulfuric acid phase was obtained with a concentration of 83.4%. The oil phase containing the DPE was shaken with 50 g of 5% sodium hydroxide solution. Separation produced 49 g of waste water with 2% sodium hydroxide. The oil phase was then shaken with 100 g of water and 4 g of sodium chloride (brine solution).

Phase separation provides:
594 g oil phase
102 g aqueous phase (carbon content 0.4 g per liter)

3. Second Distillation

The wet, yellow, cloudy oil phase obtained after washing was fractionated in a glass column 0.5 m long packed with column packing in the following way. The amount of starting material (wet) was 594 g.

| Fraction No. | Temp. in °C. Head | Bottoms | Pressure (mbar) | Weight (g) | Reflux ratio |
|---|---|---|---|---|---|
| 1 | 142–153 | 155–158 | 30 | 37 | 5:1 |
| 2 | 153 | 158 | 30 | 28 | 5:1 |
| 3 | 153 | 158 | 30 | 495 | 5:1 |
| | 154 | 161 | | | 1:1 |
| Residue | | | | 23 | |
| Cold trap | | | | 2 | |
| | | | Total = | 585 | |

GC analyses of fractions 1 to 3 show the following contents of DPE and BBZ:

| Fraction No. | DPE | BBZ |
|---|---|---|
| 1 | 53.0 | 0.2 |
| 2 | 67.6 | 0.3 |
| 3 | 86.0 | 2.0 |

Fractions 1 and 2 had unpleasant off-odors and were discarded. The main run, fraction 3, had a good fragrance quality. The yield of this odorant with a DPE content of greater than 85 wt. % and with good odor was about 30 wt. % based on the residue from ethylbenzene production used as the starting material.

Obviously, numerous modifications and variations of the present invention are possible in light of the above teachings. It is therefore to be understood that within the scope of the appended claims, the invention may be practiced otherwise than as specifically described herein.

What is new and desired to be secured by Letters Patent of the United States is:

1. A process for the purification of a 1,1-diphenylethane product with improved fragrance quality from a distillation residue of ethylbenzene production, comprising the steps of:
    subjecting the distillation residue of ethylbenzene production to a first distillation to obtain a distillate comprising 1,1-diphenylethane;
    washing said distillate with concentrated sulfuric acid at a temperature in the range of about −10° to +50° C.;
    separating the sulfuric acid phase from an oil phase;
    washing the oil phase with an aqueous solution of an alkali metal hydroxide followed by washing with water; and
    subjecting the washed oil phase to a second distillation so that a 1,1-diphenylethane product comprising greater than 85% by wt. 1,1-diphenylethane having improved fragrance quality is obtained.

2. The process of claim 1, wherein the washing with sulfuric acid is carried out at about 2° to 20° C.

3. The process of claim 1, wherein the washing with sulfuric acid is carried out for about 10 minutes to 5 hours.

4. The process of claim 3, wherein the washing with sulfuric acid is carried out for about 1 to 2 hours.

5. The process of claim 1, wherein said concentrated sulfuric acid is about 85–95 wt. % sulfuric acid.

6. The process of claim 1, wherein said aqueous solution of an alkali metal hydroxide solution comprises a solution of sodium hydroxide.

7. The process of claim 1, wherein said aqueous solution of an alkali metal hydroxide solution comprises 1-25 wt. % alkali metal hydroxide.

8. The process of claim 1, wherein said distillation residue comprises at least 60 wt. % 1,1-diphenylethane.

9. The process of claim 1, wherein said distillation residue comprises at least 80 wt. % 1,1-diphenylethane.

10. The process of claim 1, wherein the first and second distilling steps are conducted at a vacuum of about 1-200 mbar.

11. The process of claim 1, wherein said first and second distilling steps are conducted using packed distillation columns.

12. The process of claim 1, wherein said oil phase is further washed with a brine solution.

13. The process of claim 1, wherein said distillate comprises 60-90 wt. % 1,1-diphenylethane.

* * * * *